US008454806B2

(12) United States Patent
Jung et al.

(10) Patent No.: US 8,454,806 B2
(45) Date of Patent: Jun. 4, 2013

(54) SYSTEMS FOR FORMING REAGENT WITH REDUCED BACKGROUND CURRENT

(75) Inventors: Sung-Kwon Jung, Granger, IN (US); Steven C. Charlton, Osceola, IN (US); Dijia Huang, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 988 days.

(21) Appl. No.: 12/316,105

(22) Filed: Dec. 9, 2008

(65) Prior Publication Data

US 2009/0148593 A1 Jun. 11, 2009

Related U.S. Application Data

(60) Provisional application No. 61/007,184, filed on Dec. 10, 2007.

(51) Int. Cl.
*C25B 9/00* (2006.01)
*G01N 33/487* (2006.01)

(52) U.S. Cl.
USPC ....... 204/242; 204/403.01; 205/687; 422/401

(58) Field of Classification Search
USPC ................ 204/275.1, 403.01, 411, 412, 242, 204/403.02, 403.03, 403.04; 205/701, 687; 422/400, 401, 407
See application file for complete search history.

(56) References Cited

U.S. PATENT DOCUMENTS

| | | | | |
|---|---|---|---|---|
| 3,367,849 | A | 2/1968 | Blaedel et al. | |
| 4,974,592 | A * | 12/1990 | Branco | 204/411 |
| 5,989,396 | A * | 11/1999 | Prasnikar et al. | 204/252 |
| 6,551,494 | B1 | 4/2003 | Feldman et al. | 104/777.5 |
| 6,576,101 | B1 * | 6/2003 | Heller et al. | 204/403.14 |
| 2006/0000709 | A1 * | 1/2006 | Bohm et al. | 204/403.01 |

FOREIGN PATENT DOCUMENTS

| | | |
|---|---|---|
| EP | 0 342 820 A | 9/1993 |
| EP | 0 800 086 B1 | 1/2003 |
| WO | WO 2007/058999 | 5/2007 |

OTHER PUBLICATIONS

PCT Search Report for International Application No. PCT/US2004/019796 dated Jan. 4, 2009 (5 pages).

PCT Written Opinion for International Application No. PCT/US2008/085818 dated Jan. 4, 2009 (4 pages).

* cited by examiner

*Primary Examiner* — Keith Hendricks
*Assistant Examiner* — Steven A. Friday
(74) *Attorney, Agent, or Firm* — Nixon Peabody LLP

(57) ABSTRACT

Systems and methods for electrochemically oxidizing components of a test-sensor reagent prior to deposition on a test sensor comprise at least a first electrode and a second electrode for contacting the test-sensor reagent. The first electrode and the second electrode may have hollow interior portions for contacting the test-sensor reagent to produce a modified test-sensor reagent having a reduced background current.

13 Claims, 8 Drawing Sheets

SYSTEMS FOR FORMING REAGENT WITH REDUCED BACKGROUND CURRENT

CROSS REFERENCE TO RELATED APPLICATION

This application claims priority to Application No. 61/007,184 filed on Dec. 10, 2007 which is incorporated by reference in its entirety.

FIELD OF THE INVENTION

The present invention relates generally to systems and methods for modifying a test sensor reagent. More specifically, the present invention relates to systems and methods for oxidizing a test sensor reagent via an electrochemical system prior to the deposition of the reagent on a test sensor.

BACKGROUND OF THE INVENTION

The quantitative determination of analytes in body fluids is of great importance in the diagnoses and maintenance of certain physiological abnormalities. For example, blood glucose, hemoglobin (Hb), hemoglobin $A1_C$ ($Hb_{A1c}$), lactate, cholesterol, bilirubin, and other analytes should be monitored in certain individuals. In particular, it is important that individuals who are diabetic frequently check the glucose level in their body fluids to regulate the glucose intake in their diets. The results of these analyte tests. may be used to determine what, if any, insulin or other medication should be administered.

In one type of testing system, test sensors are used to test a fluid, such as a sample of blood. The test sensor contains biosensing or reagent material that will react with the analyte of interest, such as blood glucose. The testing end of the test sensor is adapted to be placed into the fluid being tested, for example, blood that has accumulated on a person's finger after the finger has been pricked. A sufficient amount of fluid to be tested is drawn by capillary action into a capillary channel that extends in the test sensor from the testing end to the reagent material. In some test sensors, the fluid then chemically reacts with the reagent material in the test sensor resulting in an electrical signal indicative of the analyte level in the fluid being tested.

One problem with current test sensors is that the reagent material may contain components that produce an undesirable background current or signal. The background current may affect the accuracy and precision of the testing results, as well as the stability of the testing system. The background current may result from impurities in the components of the reagent or from the components themselves. Thus, it would be desirable to have a test sensor reagent that improves test sensor accuracy, precision and stability by reducing the background current. Furthermore, by reducing the background current, at least one of the parameters (i.e., the intercept value) involved in the calibration process may be reduced or eliminated which will reduce the effort necessary to provide calibration information for a particular lot of test sensors and will be beneficial to users who will have less information to input for calibration purposes.

SUMMARY OF THE INVENTION

In one embodiment, a method for the electrochemical oxidation of a test-sensor reagent comprises the acts of providing the test-sensor reagent having oxidizable species and flowing the test-sensor reagent through a system having a first electrode and a second electrode. A reduction reaction may occur at the first electrode and an oxidation reaction may occur at the second electrode. The method further comprises applying a current to at least one of the first or second electrode and oxidizing the oxidizable species so as to produce a modified test-sensor reagent with a reduced background current.

In another embodiment, a system for electrochemically oxidizing components of a test-sensor reagent prior to deposition on a test sensor comprises a receptacle for holding an amount of the test-sensor reagent. The system also comprises a first electrode and a second electrode for contacting the test-sensor reagent. The first electrode and the second electrode have hollow interior portions. Oxidation occurs at at least one of the first electrode or the second electrode to produce a modified test-sensor reagent having a reduced background current.

According to another embodiment, a method for forming a test sensor comprises the acts of providing a base, a second layer and a plurality of electrodes. The base and the second layer assist in forming a channel for receiving a fluid sample. The method further comprises placing a modified reagent on the test sensor in close relationship with at least one of the plurality of electrodes. The modified reagent having been oxidized to reduce the background current thereof.

Figure 1A:
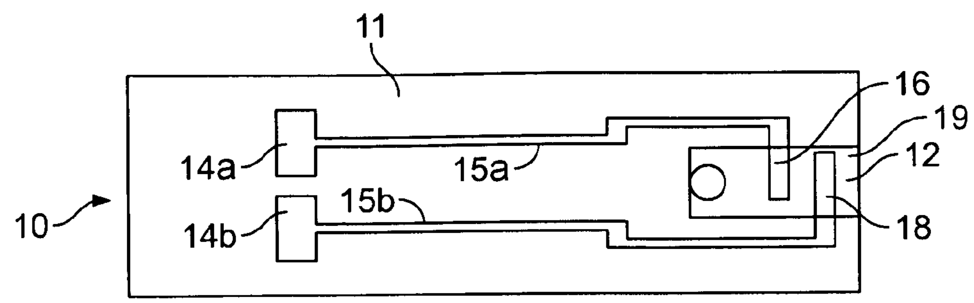
FIG. 1A is a top view of a test sensor.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF ILLUSTRATED EMBODIMENTS

A test sensor is typically adapted to receive a fluid sample, which an instrument or meter subsequently analyzes to produce a concentration reading. Some analytes that may be measured include blood glucose, lipid profiles (e.g., cholesterol, triglycerides, LDL, and HDL), microalbumin, hemoglobin (Hb), hemoglobin $A1_C$ fructose, lactate, or bilirubin. It is contemplated that other analyte concentrations, in addition to those mentioned above, may be determined. The analytes may be in, for example, a whole blood sample, a blood serum sample, a blood plasma sample, other body fluids such as ISF (interstitial fluid), creatinine, urea, urine, and non-body fluids.

The test sensors may be electrochemical test sensors. One non-limiting example of an electrochemical test sensor is shown in FIG. 1A. FIG. 1A depicts a test sensor 10 including a base 11, a capillary channel, and a plurality of electrodes 16 and 18. A region 12 shows an area that defines the capillary channel (e.g., after a lid is placed over the base 11). The plurality of electrodes includes a counter electrode 16 and a working (measuring) electrode 18. In some embodiment, the electrochemical test sensor may contain at least three electrodes, such as a working electrode, an auxiliary or counter electrode, a reference electrode, a trigger electrode, or a hematocrit electrode. The electrodes may be made from a variety of conductive materials including, but not limited to, carbon, gold, platinum, palladium, ruthenium, rhodium or combinations thereof.

The electrodes 16, 18 are coupled to a plurality of conductive leads 15*a,b* which, in the illustrated embodiment, terminates with a larger area designated as a test-sensor contact 14*a,b*. The capillary channel is generally located in a fluid-receiving area 19. In addition to electrochemical test sensor, it is contemplated that other test sensors may be employed with the embodiments of the present invention. For example, test sensors having optical analysis systems to determine information related to the analyte (e.g., the analyte concentration) may be used with the concepts described herein.

Figure 1B:
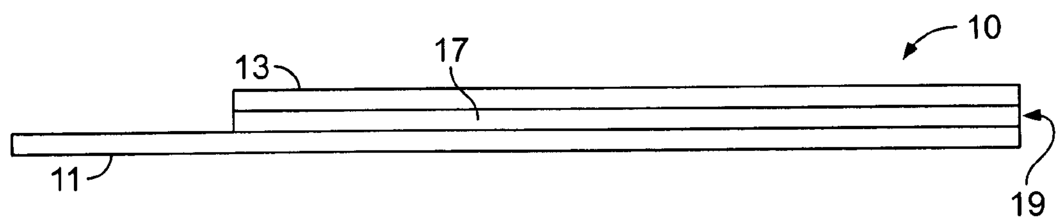
FIG. 1B is a side view of a test sensor.

Referring to FIG. 1B, a side view of the test sensor 10 of FIG. 1A is shown. As shown in FIG. 1B, the test sensor 10 may further include a lid 13 and a spacer 17. The base 11, the lid 13, and the spacer 17 may be made from a variety of materials, such as polymeric materials. Non-limiting examples of polymeric materials that may be used to form the base 11, the lid 13, and the spacer 17 include polycarbonate, polyethylene terephthalate (PET), polystyrene, polyethylene naphthalate (PEN), polyimide, and combinations thereof. It is contemplated that other materials may be used in forming the base 11, the lid 13, and/or the spacer 17.

To form the test sensor 10 of FIGS. 1A and 1B, the base 11, the spacer 17 and the lid 13 are attached by, for example, an adhesive or heat sealing. When the base 11, the lid 13, and the spacer 17 are attached, the fluid-receiving area 19 is formed. The fluid-receiving area 19 provides a flow path for introducing the fluid sample into the test sensor 10. The fluid-receiving area 19 is formed at a first end or testing end of the test sensor 10. Test sensors of the embodiments of the present invention may be formed with a base and a lid in the absence of a spacer, where the fluid-receiving area is formed directly in the base and/or the lid.

The fluid-receiving area 19 includes at least one reagent for converting the analyte of interest (e.g., glucose) in the fluid sample (e.g., blood) into a chemical species that is electrochemically measurable, in terms of the electrical current it produces, by the components of the electrode pattern. When a fluid sample (e.g., blood) is applied to the fluid-receiving area 19, the fluid sample reacts with the at least one reagent. After reacting with the reagent and in conjunction with the plurality of electrodes, the fluid sample produces electrical signals that assist in determining the analyte concentration. The conductive leads 15*a,b* carry the electrical signal back toward a second opposing end of the test sensor 10 where the test-sensor contacts 14*a,b* transfer the electrical signals to the meter (not shown).

The reagent typically includes an analyte-specific enzyme that reacts with the analyte and with an electron acceptor to produce an electrochemically measurable species that may be detected by the electrodes. The specific enzyme present in the reagent depends on the particular analyte for which the test sensor is designed to detect, where representative enzymes include: glucose oxidase, glucose dehydrogenase, cholesterol esterase, cholesterol oxidase, cholesterol dehydrogenase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many embodiments where the analyte of interest is glucose, the enzyme component of the redox reagent system is a glucose-oxidizing enzyme, e.g. a glucose oxidase or glucose dehydrogenase.

The reagent may also include mediators or other substances that assist in transferring electrons between the analyte and the conductor. The electron transfer mediator may include one or more mediator agents. Many different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, 3-phenylimino-3H-phenothiazines, 3-phenylimino-3H-phenoxazines and the like. In those embodiments, where glucose is the analyte of interest and glucose oxidase or glucose dehydrogenase are the enzyme components, mediators of particular interest are ferricyanide.

Other components that may be present in the reagent include buffering agents (e.g. citraconate, citrate, malic, maleic and phosphate) and binders (e.g., cellulose polymers). Yet other components that may be present include divalent cations, such as calcium chloride and magnesium chloride, co-enzymes such as pyrroloquinoline quinine (PQQ), flavin adenine dinucleotide (FAD) and nicotinamide adenine dinucleotide (phosphate) (NAD(P)), surfactants such as Triton®, Macol®, Tetronic®, Silwet®, Zonyl®, and Pluronic®, and stabilizing agents such as albumin, sucrose, trehalose, mannitol, and lactose.

Some of the reagent materials described above may include impurities that may affect the performance of the test sensor. Specifically, such impurities may produce a background current that affects the accuracy, precision and the stability of the test sensor. Furthermore, some of the reagent materials themselves may produce a background current that may affect the accuracy, precision and stability of the test sensor. The present invention is directed to systems and methods for reducing the background current of a test sensor reagent.

Figure 2:
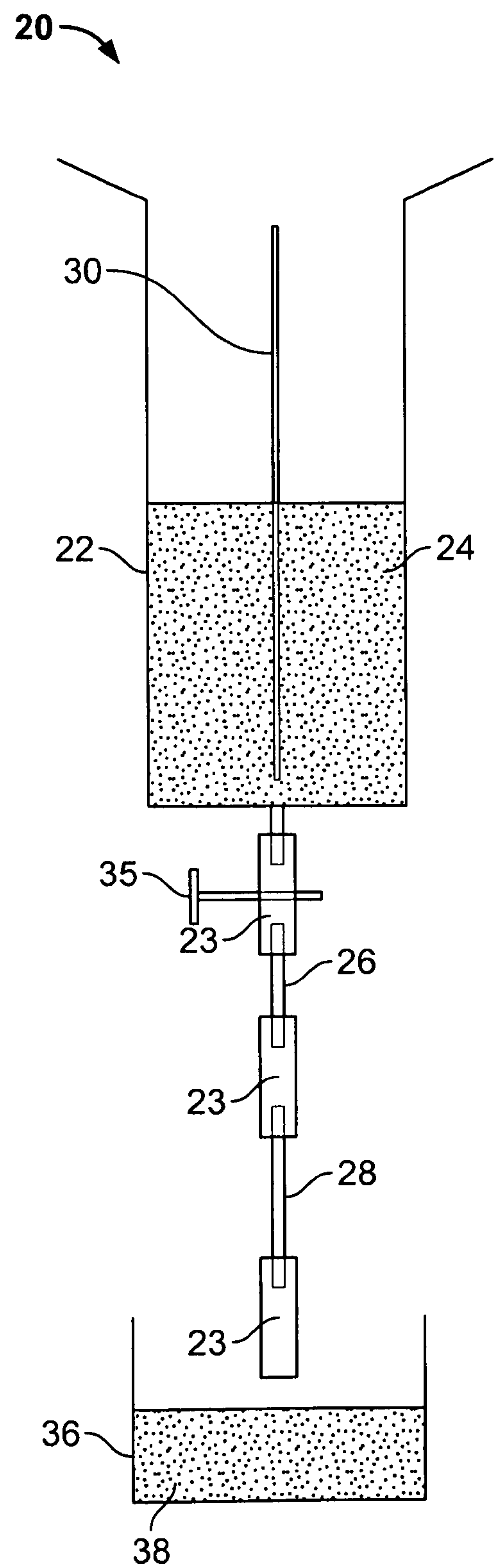
FIG. 2 is a side view of an apparatus for electrochemically oxidizing a test-sensor reagent according to one embodiment.

One embodiment of the system is shown in FIG. 2. In this figure, an apparatus 20 includes a receptacle or column 22 containing the pre-oxidized reagent material 24 (i.e., reagent material that has not yet undergone oxidation to reduce the background current). A pre-oxidized reagent material 24 is directed to flow from the column 22, through the tubing 23 that is connected to the column 22 and to a sequence of electrodes. As described in more detail below, the electrodes may have a hollow interior such that the pre-oxidized reagent material 24 flows through the interior of the electrodes. The tubing 23 may comprise a clear rigid or semi-rigid plastic material, such as polyvinyl chloride (PVC), Tygon®, Teflon® and other similar materials. The column 22 may comprise glass, polycarbonate, polystyrene and other similar materials.

In the embodiment shown in FIG. 2, the sequence of electrodes includes a first electrode 26 followed by a second electrode 28. In some embodiments, the first electrode 26 may be a counter electrode and the second electrode 28 may be a working electrode. The first electrode 26 and the second electrode 28 may be made from a variety of conductive materials, including platinum, carbon, gold, palladium, ruthenium, rhodium or combinations thereof. In some embodiments, a third electrode 30 may also be included in the system 20. The third electrode 30 may be a reference or other type of electrode. In the embodiment shown in FIG. 2, the third electrode 30 is positioned inside of the column 22 containing the pre-oxidized reagent material 24. The third electrode 30 may be comprised of silver and/or silver chloride, mercury chloride, or other similar materials. In some embodiments, the first electrode 26 and the third electrode 30 may be combined as a single electrode.

Figure 3:
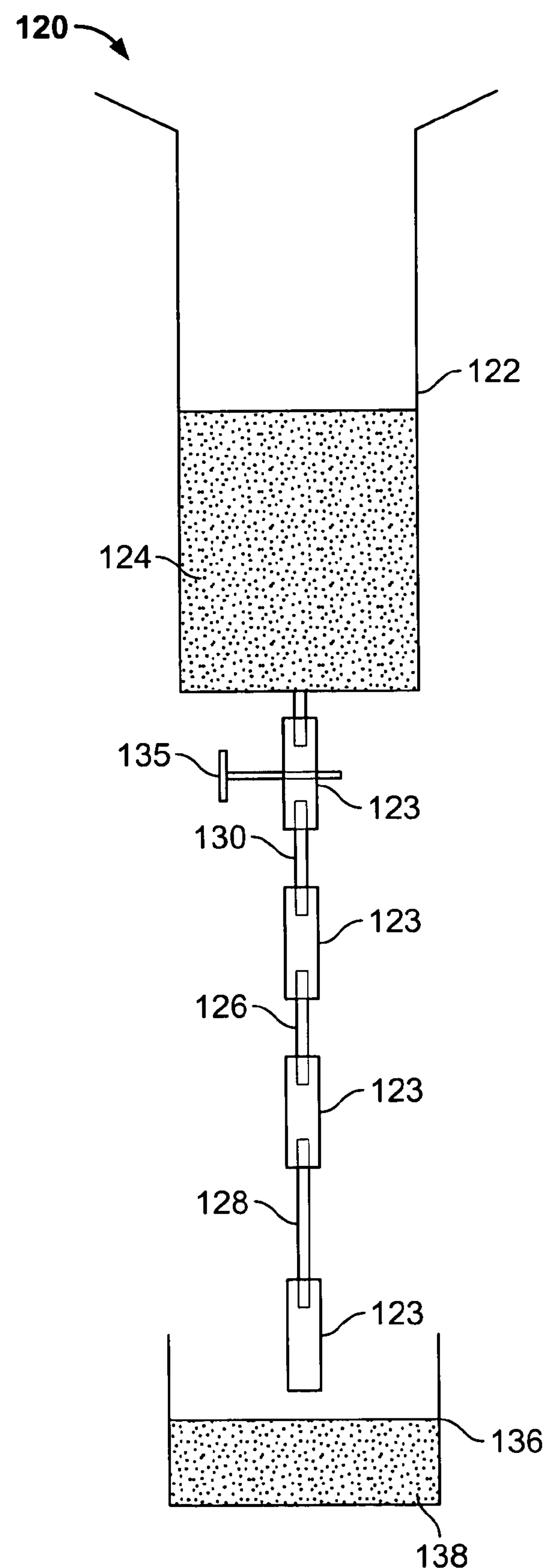
FIG. 3 is a side view of an apparatus for electrochemically oxidizing a test-sensor reagent according to another embodiment.

In an alternative embodiment shown in FIG. 3, the system 120 operates in the same manner as described with respect to FIG. 2 to oxidize the reagent to reduce the background current. However, in the embodiment depicted in FIG. 3, a third electrode 130 is positioned external to a column 122, for example, in a position preceding a first electrode 126 and a second electrode 128 in the electrode sequence. In this embodiment, the first electrode 126 may be a counter electrode, the second electrode 128 may be a working electrode and the third electrode 130 may be a reference electrode. In other embodiments, the first electrode 126 and the second electrode 130 may be combined as a single electrode.

Referring to the embodiment shown in FIG. 2, but also applicable to the embodiment shown in FIG. 3, to control the flow of the pre-oxidized reagent material 24, a valve 35 may be connected to the tubing 23 positioned below the lower end of the column 22. The valve 35 allows the user to regulate the flow of the pre-oxidized reagent material 24 as it flows from the column 22 through the tubing 23 and the sequence of electrodes. A container 36 receives the oxidized reagent material 38, which is ready to be deposited on a test sensor 10. The flow to the container 36 may occur due to gravity or by forced flow. In some situations, it is desirable to use forced flow to be able to control the flow of the pre-oxidized reagent material 24 in a more consistent manner. This is particularly preferred when small amounts of pre-oxidized reagent material 24 are being oxidized by the systems and methods described herein. This can be accomplished using a motorized syringe, for example.

Figure 4:
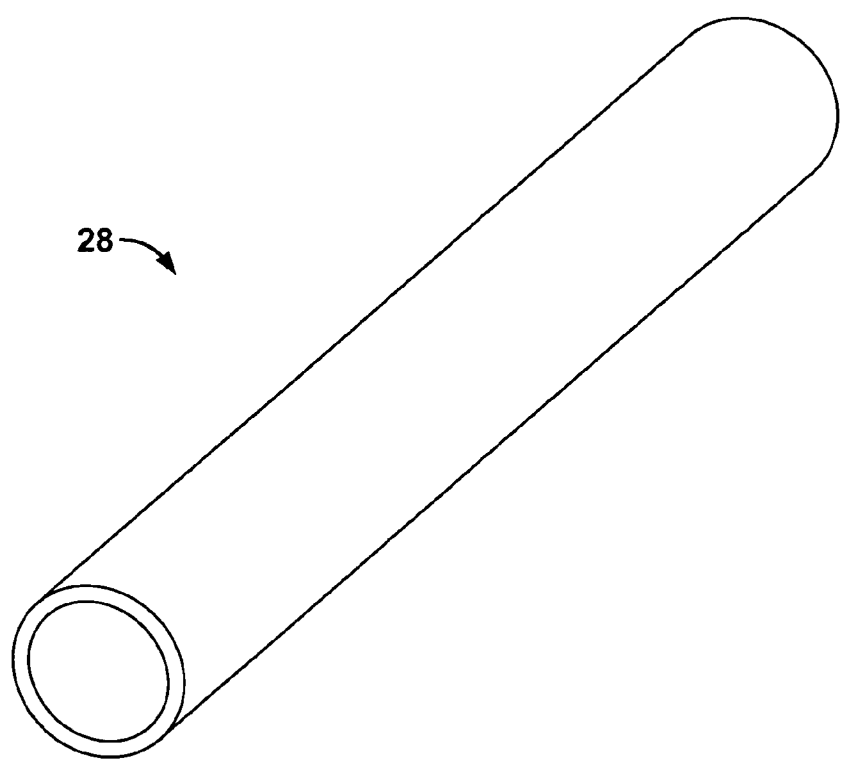
FIG. 4 is a perspective view of an electrode that may be used in the apparatus of FIGS. 2 and 3.

In one aspect of the embodiments described herein and shown in FIG. 4, the electrodes are cylindrical, hollow electrodes such that the pre-oxidized reagent material flows through the interior of the electrodes. The electrode shown in FIG. 4 is labeled as the second electrode 28; however, the electrode shown in FIG. 4 may also represent electrodes in other embodiments, e.g., the second electrode 128, or other types of electrodes, e.g., the first electrode 26, 126 and the third electrode 30, 130. In some embodiments, one or more of the electrodes may not be hollow, such as the third electrode 30 in FIG. 2, but may instead have a solid interior portion.

In some embodiments, the inner surface of the third electrode 30, 130 (and first electrode if combined with the third electrode) may be modified by chlorination, such as by anodizing the electrode in a hydrogen chloride solution and then applying a voltage. The resulting chlorination results in the deposition of silver chloride on the inner surface. The presence of the hollow electrodes in the systems described herein is an important feature because the contact of the reagent molecules with the inner portion of the electrodes allows for the oxidation reactions to occur in a more efficient manner. Where typically the electrodes are planar or rod-like, it would be necessary to stir the reagent so that all portions of the reagent come into contact with the electrodes. Such stirring would be required for a long period of time since the oxidation would only occur at the surface of the electrodes. The use of hollow electrodes in the present systems allows for the pre-oxidized reagent material to contact the electrodes in a manner that allows the oxidation process to occur more efficiently and faster. The inner diameter of the electrodes, i.e., the first electrode, 26, 126, the second electrode 28, 128 and the third electrode 30, 130, may range from about 0.1 mm to about 2 mm, and preferably from about 0.5 mm to about 1 mm.

Referring to FIG. 2 (and also applicable to FIG. 3), according to one embodiment, a pre-oxidized reagent material 24 is added to the column 22 of the apparatus 20 and is allowed to flow through the electrode sequence. A voltage, e.g., 600 mV, is applied to the second electrode 28 and any oxidizable species, which may be present as impurities from the components of the pre-oxidized reagent materials 24 or as the components themselves, are oxidized at the second electrode 28. The oxidation reactions that occur at the second electrode 28 may depend on the components of the pre-oxidized reagent material 24. For example, where the pre-oxidized reagent material 24 includes a ferricyanide mediator and certain amino acids of glucose dehydrogenase, the following reactions may occur:

$$Fe^{2+} \rightarrow Fe^{3+}$$

$$\text{Amino acid}_{red} \rightarrow \text{amino acid}_{ox}$$

As described herein, the background current may be removed by the following reaction that takes place at the second electrode 28:

$$2Fe^{2+} \rightarrow 2Fe^{3+} + 2e^-$$

The following coupled reaction may occur at the first electrode 26:

$$2H_2O + 2e^- \rightarrow H_2 + 2OH^-$$

Thus, one example of an overall reaction may be represented as:

$$2Fe^{2+} + 2H_2O \rightarrow 2Fe^{3+} + H_2 + 2OH^-$$

In accordance with the present invention, by passing the pre-oxidized reagent material 24 through the sequence of electrodes, several of the species that may cause an increase in the background current are oxidized such that they are no longer available to contribute to the background current. Furthermore, any oxidizable impurities that are present in the pre-oxidized reagent material 24 will be oxidized, which further reduces the level of the background current. Thus, many other reactions, in addition to those described herein, may occur as a result of the oxidation of the reagent material.

EXAMPLE 1

According to one example, a pre-oxidized reagent material was run through the apparatus and the effectiveness of the pre-oxidation process was measured. The pre-oxidized reagent material had the following composition:

| INGREDIENT | WT. % |
|---|---|
| Nanopure Water | 40 |
| 4 wt. % hydroxylethyl cellulose (HEC) | 4.5 |
| 200 mM citrate buffer (pH 5.0) | 50 |
| Potassium ferricyanide (mediator) | 4.8 |
| Mega 8 (surfactant) | 0.2 |
| FAD-GDH (205 U/mg) FAD-dependent glucose dehydrogenase (enzyme) | 0.5 |

The reagent composition was prepared according to the formulation in the table, however it will be understood that other formulations containing different enzymes, mediators, binders, etc. known in the art may be used with the systems and methods described herein. Furthermore, the components of the reagent may be present in different amounts from those shown in the table and such formulations may also be used with the systems and methods described herein.

Figure 5:
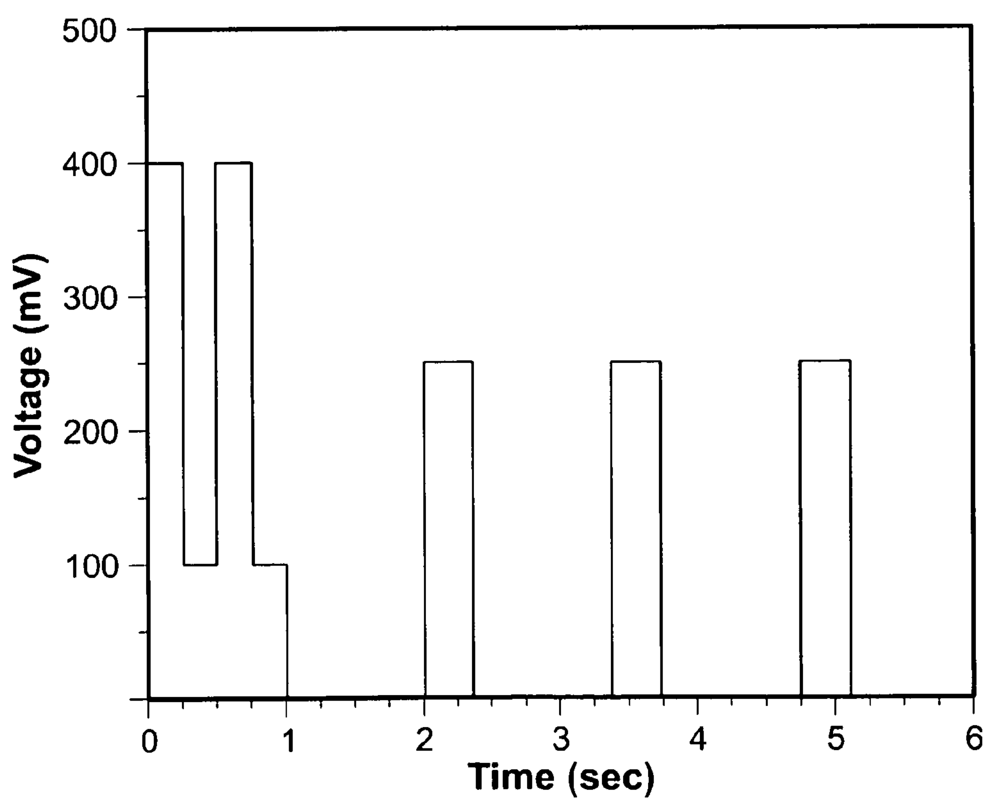
FIG. 5 is a graph that depicts the testing sequence for testing the effectiveness of the oxidation of the reagent.

After running the formulation through the apparatus and system described herein to oxidize the species present in the formulation, the oxidized reagent formulation was applied to a test sensor, such as shown in FIG. 1. A test sequence was performed according to the sequence shown in FIG. 5. In this example, a sequence of voltages was applied to a set of test sensors, ranging from 0 mV to 400 mV. Specifically, the test sequence was applied according to the following sequence: 400 mV, 100 mV, 400 mV, 100 mV, pause (0 mV), 250 mV, pause (0 mV), 250 mV, pause (0 mV), 25 mV, over a time period of about 5 seconds. It is contemplated that different test sequences may be used that apply higher and lower voltages and at different intervals than those shown in FIG. 5.

Figure 6:
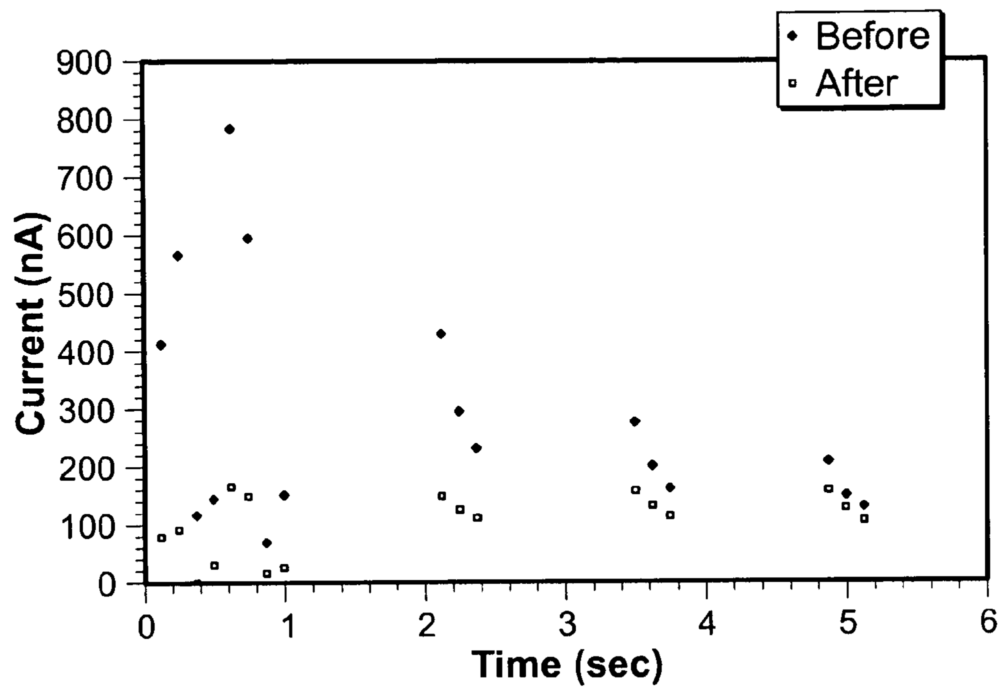
FIG. 6 is graph that depicts the background current before and after oxidation of the reagent.

After the test sequence was applied, the background currents were measured and compared with measurements of background currents that were taken before the test-sensor reagent was oxidized using the present systems and test methods. A comparison of the measurements is shown in FIG. 6. For all cases shown, the background currents of the test sensors having oxidized reagent materials were lower than the background currents of the test sensors having reagent materials that were non-oxidized.

Figure 7:
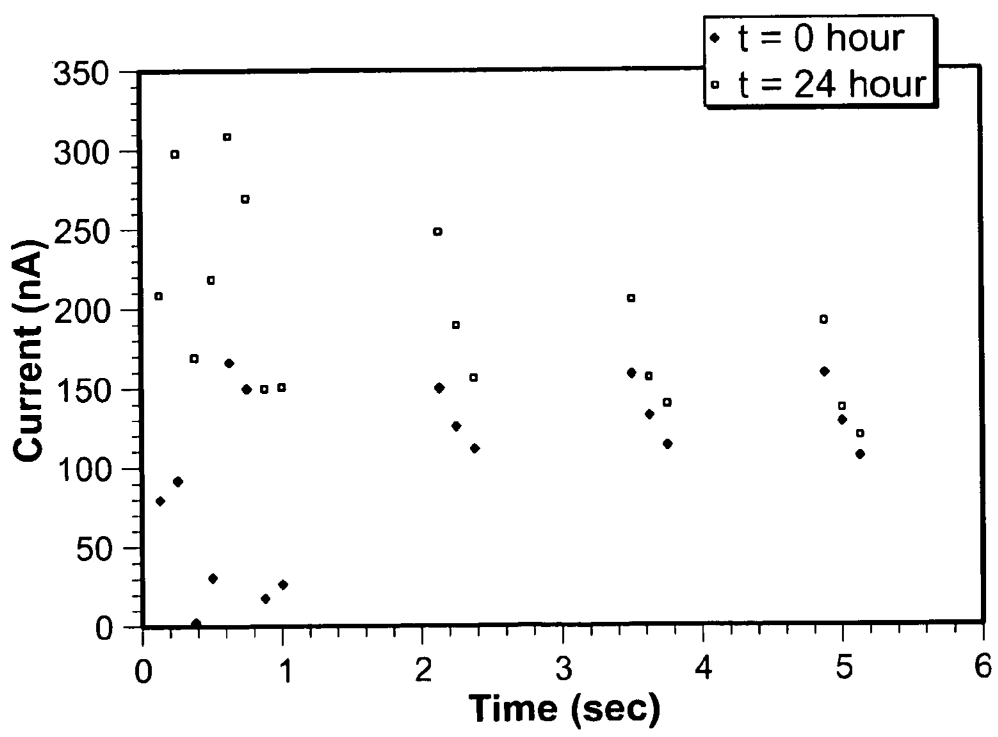
FIG. 7 is a graph that depicts the change in background current with time before and after oxidation of the reagent.

Other tests were performed to measure the effect of time on the level of background currents tested. In one such test, shown in FIG. 7, it was determined that the background currents of the oxidized reagent materials increased over time. Specifically, the background currents were measured twenty-four hours after initial measurements were made and, in all cases, the background current increased over the twenty-four hour time period. These results indicate that to maintain a lower background current, the oxidized reagent should be promptly deposited on the test sensor.

In addition to reducing the background current to improve the accuracy, precision and stability of the reagent, reducing the background current may also eliminate or reduce some of the effort necessary to provide calibration information for a particular lot of test sensors. For each lot of test sensors, a slope value and an intercept value of the dose response line are determined. The intercept value is related to the amount of background current that occurs due to the non-oxidized reagent. It is desirable that the intercept value be as low as possible. This is particularly important for the accurate measurement of fluid samples with low glucose levels. Due to oxidation of the reagent material according to the present invention, the intercept (and background current) values will be small or even negligible. Thus, the coding of the test sensors would, in effect, only require a "one parameter" effort (for the slope value), which would greatly simplify and increase the accuracy of the calibration process. If only a limited number of calibration codes are available, they may all be applied to variations in the slope, hence the resolution can be finer and errors reduced that are attributable to assignment to one of the available slopes.

Furthermore, if the slope value can be adjusted by, for example, controlling the working electrode area, then it is possible to achieve a "no-coding" system. In this context, "no coding" means that the calibration line is fixed and that no adjustments to the slope and intercept are necessary for individual manufacturing lots of reagent. The adjustment of the slope value may be achieved by controlling and adjusting the working electrode area, for example, by adjusting the electrode ablation or by adjusting the spacer width. A large electrode area gives a higher (steeper) slope than a smaller electrode area. Thus, if there is a means to control the electrode area and thus the slope, and if oxidation of the reagent is available to control the intercept, then it is possible to achieve a "no-coding" system. Such a system would be beneficial to manufacturers who will have less calibration information to provide to users and to users who will have less information to input for calibration purposes.

EXAMPLE 2

According to a further example, a pre-oxidized reagent material was run through the apparatus and the effectiveness of the pre-oxidation process was measured. Specifically, the reagent below was run though a column at 600 mV as shown in for example FIG. 3. The column included an Ag/AgCl reference electrode, a Pt counter electrode and a Pt working electrode. The pre-oxidized reagent material had the following composition:

| INGREDIENT | WT. % |
|---|---|
| Nanopure water | 41.3 |
| 2 wt. % Hydroxylethyl cellulose (HEC) | 4 |
| 200 mM Sodium phosphate buffer (pH 7.0) | 50 |
| 3-(2',5'-disulfophenylimino)-3H-phenothiazine bis sodium salt. (MLB) | 4 |
| Mega 8 (surfactant) | 0.2 |
| FAD-GDH (205 U/mg) FAD-dependent glucose dehydrogenase (enzyme) | 0.5 |

After running the formulation through the apparatus and system described herein to oxidize the species present in the formulation, the oxidized reagent formulation was applied to a test sensor. A test sequence was performed according to the sequence shown in FIG. 5. In this example, a sequence of voltages was applied to a set of test sensors, ranging from 0 mV to 400 mV. Specifically, the test sequence was applied according to the following sequence: 400 mV, 100 mV, 400 mV, 100 mV, pause (0 mV), 250 mV, pause (0 mV), 250 mV, pause (0 mV), 25 mV, over a time period of about 5 seconds.

Figure 8:
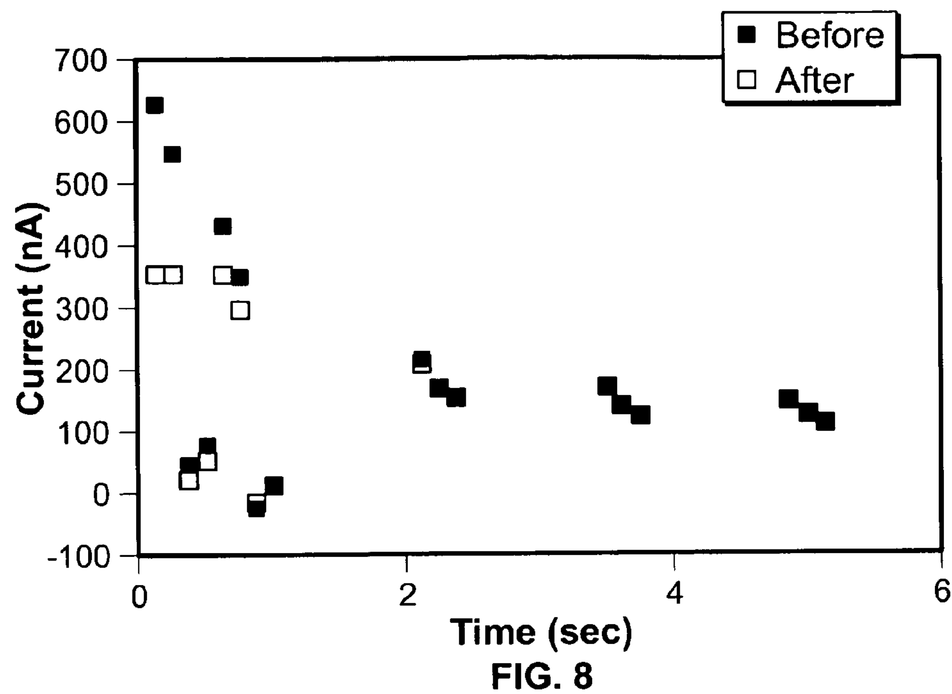
FIGS. 8-12 are graphs that depict the background current before and after oxidation of various reagents.

After the test sequence was applied, the background currents were measured and compared with measurements of background currents that were taken before the test-sensor reagent was oxidized using the present systems and test methods. A comparison of the measurements is shown in FIG. 8. For all cases shown, the background currents of the test sensors having oxidized reagent materials were lower than the background currents of the test sensors having reagent materials that were non-oxidized.

EXAMPLE 3

According to a further example, a pre-oxidized reagent material was run through the apparatus and the effectiveness of the pre-oxidation process was measured. Specifically, the reagent below was run though a column at 600 mV as shown in for example FIG. 3. The column included an Ag/AgCl reference electrode, a Pt counter electrode and a Pt working electrode. The pre-oxidized reagent material had the following composition:

| INGREDIENT | WT. % |
|---|---|
| Nanopure water | 41.3 |
| 2 wt. % Hydroxylethyl cellulose (HEC) | 4 |
| 200 mM Sodium phosphate buffer (pH 7.0) | 50 |
| Ruthenium hexamine | 4 |
| Mega 8 (surfactant) | 0.2 |
| FAD-GDH (205 U/mg) FAD-dependent glucose dehydrogenase (enzyme) | 0.5 |

After running the formulation through the apparatus and system described herein to oxidize the species present in the formulation, the oxidized reagent formulation was applied to a test sensor. A test sequence was performed according to the sequence shown in FIG. 5 as discussed above.

Figure 9:
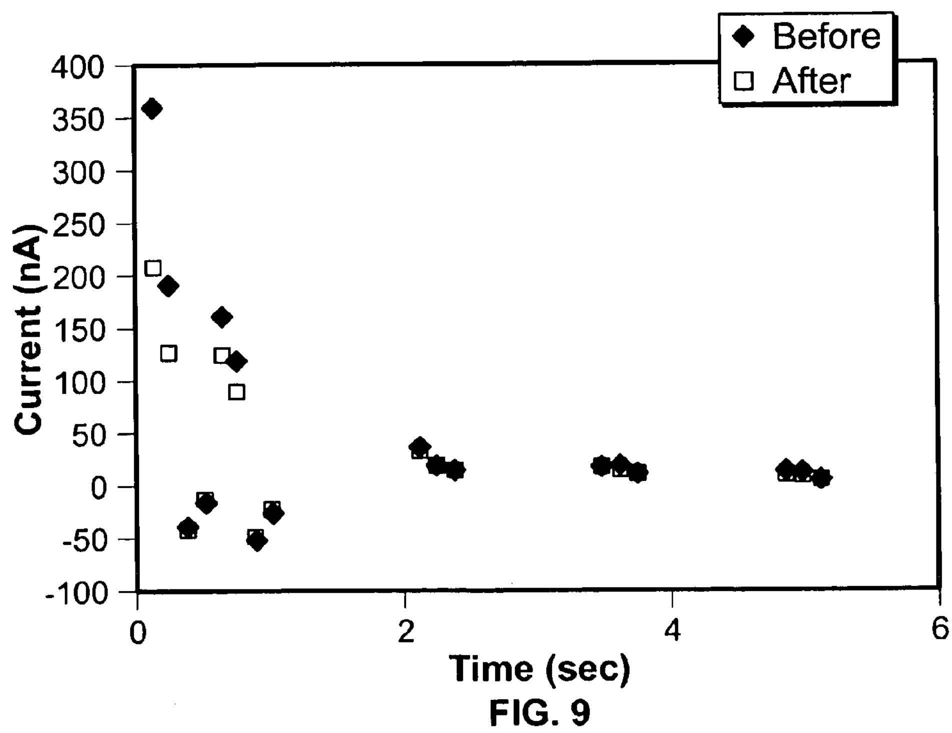

After the test sequence was applied, the background currents were measured and compared with measurements of background currents that were taken before the test-sensor reagent was oxidized using the present systems and test methods. A comparison of the measurements is shown in FIG. 9. For all cases shown, the background currents of the test sensors having oxidized reagent materials were lower than the background currents of the test sensors having reagent materials that were non-oxidized.

EXAMPLE 4

According to a further example, a pre-oxidized reagent material was run through the apparatus and the effectiveness of the pre-oxidation process was measured. Specifically, the reagent below was run though a column at 600 mV as shown in for example FIG. 3. The column included an Ag/AgCl reference electrode, a Pt counter electrode and a Pt working electrode. The pre-oxidized reagent material had the following composition:

| INGREDIENT | WT. % |
|---|---|
| Nanopure water | 41.3 |
| 2 wt. % Hydroxylethyl cellulose (HEC) | 4 |
| 200 mM Sodium phosphate buffer (pH 7.0) | 50 |
| Ruthenium hexamine | 4 |
| Mega 8 (surfactant) | 0.2 |
| Glucose oxidase (239 U/mg) (GOx) (enzyme) | 0.5 |

After running the formulation through the apparatus and system described herein to oxidize the species present in the formulation, the oxidized reagent formulation was applied to a test sensor. A test sequence was performed according to the sequence shown in FIG. 5 as discussed above.

Figure 10:
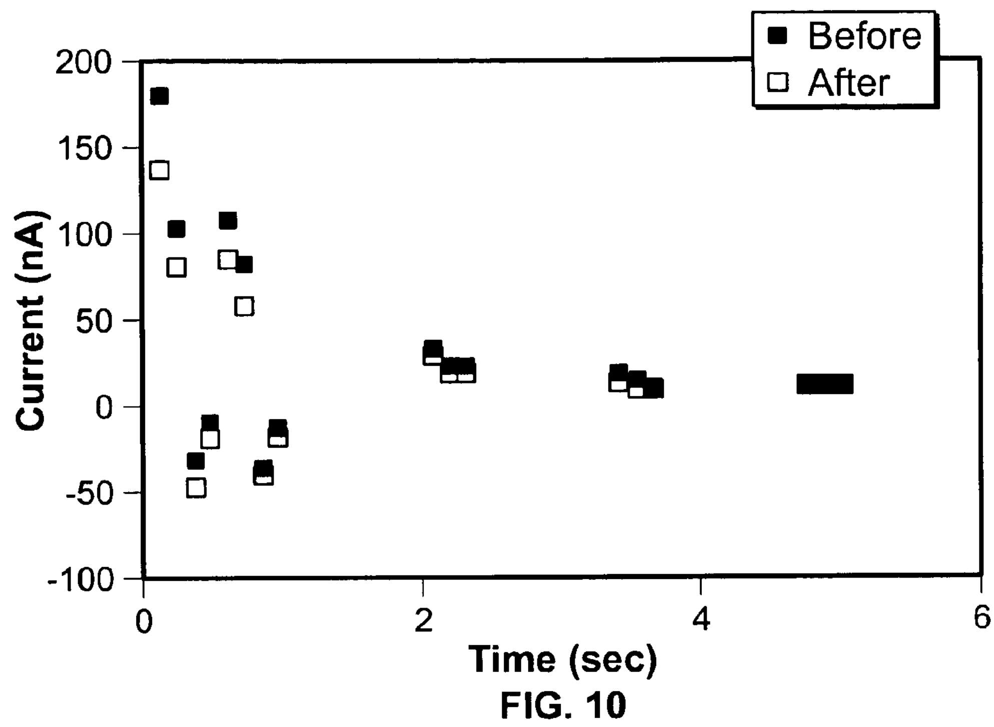

After the test sequence was applied, the background currents were measured and compared with measurements of background currents that were taken before the test-sensor reagent was oxidized using the present systems and test methods. A comparison of the measurements is shown in FIG. 10. For all cases shown, the background currents of the test sensors having oxidized reagent materials were lower than the background currents of the test sensors having reagent materials that were non-oxidized.

EXAMPLE 5

According to a further example, a pre-oxidized reagent material was run through the apparatus and the effectiveness of the pre-oxidation process was measured. Specifically, the reagent below was run though a column at 600 mV as shown in for example FIG. 3. The column included an Ag/AgCl reference electrode, a Pt counter electrode and a Pt working electrode. The pre-oxidized reagent material had the following composition:

| INGREDIENT | WT. % |
|---|---|
| Nanopure water | 41.3 |
| 2 wt. % Hydroxylethyl cellulose (HEC) | 4 |
| 200 mM Sodium Phosphate buffer (pH 7.0) | 50 |
| Ferricyanide | 4 |
| Mega 8 (surfactant) | 0.2 |
| Glucose oxidase (GOx) (239 U/mg) (enzyme) | 0.5 |

After running the formulation through the apparatus and system described herein to oxidize the species present in the formulation, the oxidized reagent formulation was applied to a test sensor. A test sequence was performed according to the sequence shown in FIG. 5 as discussed above.

Figure 11:
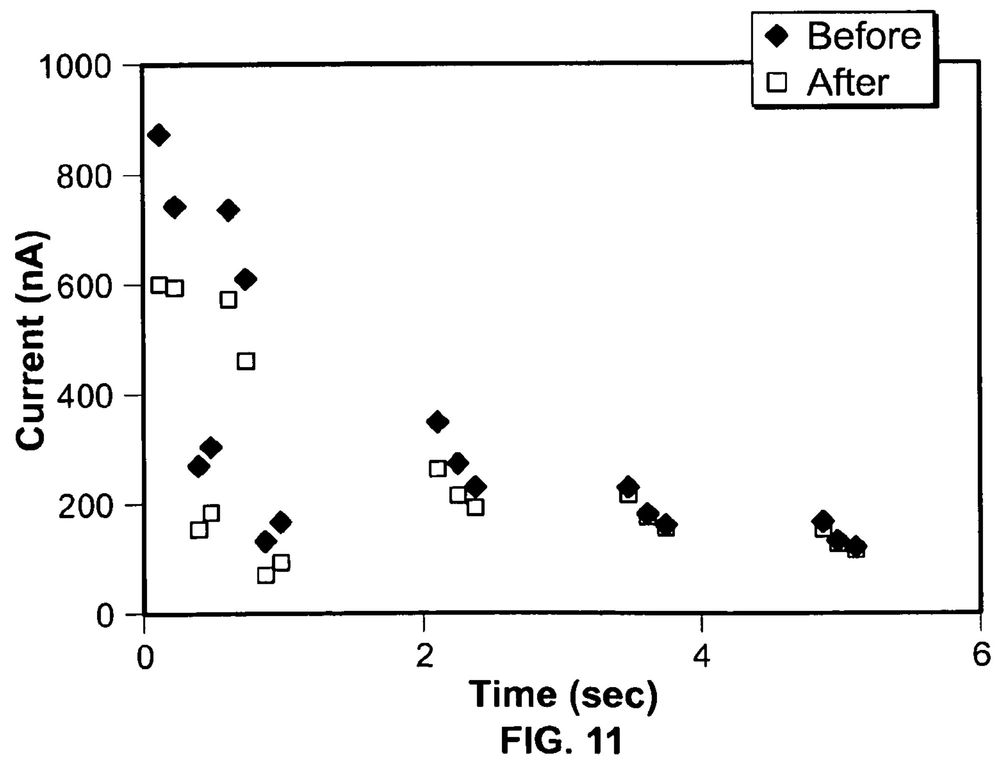

After the test sequence was applied, the background currents were measured and compared with measurements of background currents that were taken before the test-sensor reagent was oxidized using the present systems and test methods. A comparison of the measurements is shown in FIG. 11. For all cases shown, the background currents of the test sensors having oxidized reagent materials were lower than the background currents of the test sensors having reagent materials that were non-oxidized.

EXAMPLE 6

According to a further example, a pre-oxidized reagent material was run through the apparatus and the effectiveness of the pre-oxidation process was measured. Specifically, the reagent below was run though a column at 600 mV as shown in for example FIG. 3. The column included an Ag/AgCl reference electrode, a Pt counter electrode and a Pt working electrode. The pre-oxidized reagent material had the following composition:

| INGREDIENT | WT. % |
|---|---|
| Nanopure water | 41.3 |
| 2 wt. % Hydroxylethyl cellulose (HEC) | 4 |
| 200 mM Sodium Phosphate buffer (pH 7.0) | 50 |
| 3-(2',5'-disulfophenylimino)-3H-phenothiazine bis sodium salt. (MLB) | 4 |
| Mega 8 (surfactant) | 0.2 |
| Glucose oxidase (GOx) (239 U/mg) (enzyme) | 0.5 |

After running the formulation through the apparatus and system described herein to oxidize the species present in the formulation, the oxidized reagent formulation was applied to a test sensor. A test sequence was performed according to the sequence shown in FIG. 5 as discussed above.

Figure 12:
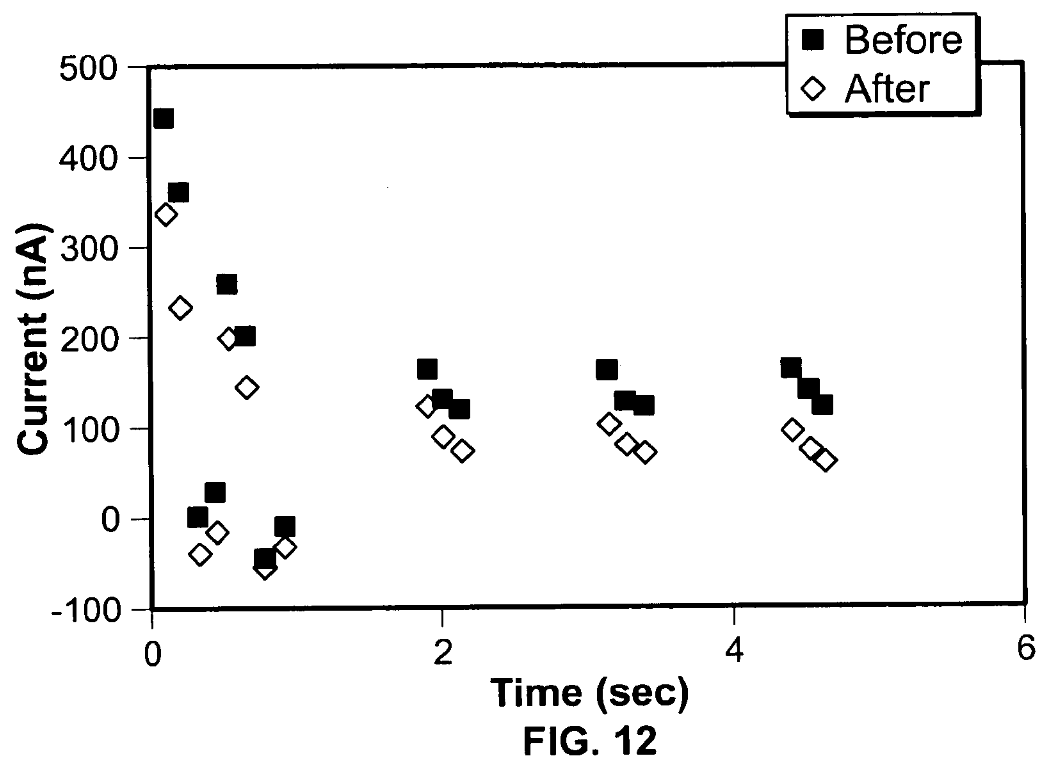

After the test sequence was applied, the background currents were measured and compared with measurements of background currents that were taken before the test-sensor reagent was oxidized using the present systems and test methods. A comparison of the measurements is shown in FIG. 12. For all cases shown, the background currents of the test sensors having oxidized reagent materials were lower than the background currents of the test sensors having reagent materials that were non-oxidized.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, and alternatives falling within the spirit and scope of the invention.

Alternative Embodiment A

A method for the electrochemical oxidation of a test-sensor reagent, the method comprising the acts of:

providing the test-sensor reagent having oxidizable species;

flowing the test-sensor reagent through a system having a first electrode and a second electrode, wherein a reduction reaction may occur at the first electrode and an oxidation reaction may occur at the second electrode;

applying a current to at least one of the first or second electrode; and oxidizing the oxidizable species so as to produce a modified test-sensor reagent with a reduced background current.

Alternative Embodiment B

The method of alternative embodiment A, wherein the first electrode is a counter electrode and comprises platinum, carbon, gold, palladium, ruthenium, rhodium or combinations thereof.

Alternative Embodiment C

The method of alternative embodiment A, wherein the second electrode is a working electrode and comprises platinum, carbon, gold, palladium, ruthenium, rhodium or combinations thereof.

Alternative Embodiment D

The method of alternative embodiment A, wherein the first electrode and the second electrode are hollow and the test-sensor reagent flows through interior portions of the first electrode and the second electrode.

Alternative Embodiment E

The method of alternative embodiment A, wherein the system further includes a third electrode.

Alternative Embodiment F

The method of alternative embodiment E, wherein the third electrode is a reference electrode and comprises silver, silver chloride, mercury chloride or combinations thereof.

Alternative Embodiment G

The method of alternative embodiment E, wherein the third electrode is hollow and the surface of an interior portion of the third electrode is modified by chlorination.

Alternative Embodiment H

The method of alternative embodiment A, wherein the oxidizable species include impurities from the components of the test sensor-reagent.

Alternative Embodiment I

The method of alternative embodiment A, wherein the oxidizable species include components of the test-sensor reagent.

Alternative Embodiment J

The method of alternative embodiment A, wherein the act of flowing the test-sensor reagent through the system occurs via gravity.

Alternative Embodiment K

The method of alternative embodiment A, wherein the act of flowing the test-sensor reagent through the system occurs by a controlled flow.

Alternative Embodiment L

A system for electrochemically oxidizing components of a test-sensor reagent prior to deposition on a test sensor, the system comprising:

a receptacle for holding an amount of the test-sensor reagent;

a first electrode and a second electrode for contacting the test-sensor reagent, the first electrode and the second electrode having hollow interior portions; and wherein oxidation occurs at at least one of the first electrode or the second electrode to produce a modified test-sensor reagent having a reduced background current.

Alternative Embodiment M

The system of alternative embodiment L, wherein the first electrode is a counter electrode and comprises platinum, carbon, gold, palladium, ruthenium, rhodium or combinations thereof.

Alternative Embodiment N

The system of alternative embodiment L, wherein the second electrode is a working electrode and comprises platinum, carbon, gold, palladium, ruthenium, rhodium or combinations thereof.

Alternative Embodiment O

The system of alternative embodiment L, further comprising a third electrode.

Alternative Embodiment P

The system of alternative embodiment O, wherein the third electrode is a reference electrode and comprises silver, silver chloride, mercury chloride or combinations thereof.

Alternative Embodiment Q

The system of alternative embodiment L, further including a valve to assist in controlling the flow of the test-sensor reagent.

Alternative Embodiment R

The system of alternative embodiment L, further including tubing for connecting the receptacle, the first electrode and the second electrode.

Alternative Embodiment S

The system of alternative embodiment L, wherein the test-sensor reagent flows through the first electrode prior to flowing through the second electrode.

Alternative Embodiment T

A method for forming a test sensor, the method comprising the acts of:

providing a base, a second layer and a plurality of electrodes, the base and the second layer assisting in forming a channel for receiving a fluid sample; and placing a modified reagent on the test sensor in close relationship with at least one of the plurality of electrodes, the modified reagent having been oxidized to reduce the background current thereof.

Alternative Embodiment U

The method of alternative embodiment T, wherein the modified reagent is prepared by flowing a test-sensor reagent through a system comprising a first electrode and a second electrode and applying a current to at least one of the first electrode or the second electrode to oxidize any oxidizable species in the test-sensor reagent.

Alternative Embodiment V

The method of alternative embodiment T, wherein second layer may be a spacer, a lid or a combination thereof.

What is claimed is:

1. A system comprising:

a receptacle including an amount of a test-sensor reagent, the test-sensor reagent including a mediator and an enzyme;

a first electrode and a second electrode for contacting the test-sensor reagent, the first electrode and the second electrode having hollow interior portions, wherein oxidation occurs at at least one of the first electrode or the second electrode to produce a modified test-sensor reagent having a reduced background current, the test-sensor reagent being directed from the receptacle to the first electrode and the second electrode through a tubing; and a test sensor for receiving the modified test-sensor reagent having a reduced background current, the test sensor including a lid and base, the lid and base assisting in forming a fluid-receiving area that provides a flow path for introducing a fluid sample.

2. The system of claim 1, wherein the first electrode is a counter electrode, the first electrode comprising platinum, carbon, gold, palladium, ruthenium, rhodium or combinations thereof.

3. The system of claim 1, wherein the second electrode is a working electrode, the working electrode comprising platinum, carbon, gold, palladium, ruthenium, rhodium or combinations thereof.

4. The system of claim 1, further comprising a third electrode.

5. The system of claim 4, wherein the third electrode is a reference electrode, the third electrode comprising silver, silver chloride, mercury chloride or combinations thereof.

6. The system of claim 1, further including a valve to assist in controlling the flow of the test-sensor reagent.

7. The system of claim 1, wherein the test-sensor reagent flows through the first electrode prior to flowing through the second electrode.

8. The system of claim 1, wherein the receptacle includes glass.

9. The system of claim 1, wherein the receptacle includes polycarbonate or polystyrene.

10. The system of claim 1, wherein the tubing comprises a clear rigid or semi-rigid plastic material.

11. The system of claim 1, wherein the test sensor is an electrochemical test sensor.

12. The system of claim 1 wherein the test sensor includes two additional electrodes.

13. The system of claim 1, wherein the test sensor is an optical test sensor.

* * * * *